(12) United States Patent
Masini

(10) Patent No.: US 9,492,280 B2
(45) Date of Patent: Nov. 15, 2016

(54) MULTIPLE-CAM, POSTERIOR-STABILIZED KNEE PROSTHESIS

(71) Applicant: MedIdea, LLC, Ann Arbor, MI (US)

(72) Inventor: Michael A. Masini, Ann Arbor, MI (US)

(73) Assignee: MedIdea, LLC, Ann Arbor, MI (US)

( * ) Notice: Subject to any disclaimer, the term of this patent is extended or adjusted under 35 U.S.C. 154(b) by 193 days.

(21) Appl. No.: 14/276,407

(22) Filed: May 13, 2014

(65) Prior Publication Data

US 2014/0249640 A1    Sep. 4, 2014

Related U.S. Application Data

(60) Continuation of application No. 12/337,280, filed on Dec. 17, 2008, now Pat. No. 8,721,730, which is a continuation of application No. 10/430,548, filed on May 6, 2003, now Pat. No. 8,273,132, which is a division of application No. 09/724,100, filed on Nov. 28, 2000, now Pat. No. 6,558,426.

(51) Int. Cl.
*A61F 2/38*    (2006.01)

(52) U.S. Cl.
CPC ........... *A61F 2/3836* (2013.01); *A61F 2/3886* (2013.01)

(58) Field of Classification Search
CPC .......................................... A61F 2/3836–2/389
USPC ................................ 623/20.14, 20.26, 20.27
See application file for complete search history.

(56) References Cited

U.S. PATENT DOCUMENTS

| 3,765,033 A | 10/1973 | Goldberg et al. |
| 3,840,905 A * | 10/1974 | Deane ................... A61F 2/3886 623/20.27 |
| 3,852,045 A | 12/1974 | Wheeler et al. |

(Continued)

FOREIGN PATENT DOCUMENTS

| DE | 4308563 A1 | 9/1994 |
| DE | 19529824 A1 | 2/1997 |

(Continued)

OTHER PUBLICATIONS

Andriacchi, T.P., "The Effect of Knee Kinematics, Gait and Wear on the Short- and Long-Term Outcomes of Primary Total Knee Replacement," NIH Consensus Development Conference on Total Knee Replacement, pp. 61-64, Dec. 8-10, 2003, (4 pages).

(Continued)

*Primary Examiner* — Christopher D Prone
(74) *Attorney, Agent, or Firm* — Dinsmore & Shohl LLP

(57) ABSTRACT

A total knee replacement system includes a tibial component having a tibial post with a posterior portion, and a femoral component with medial and lateral condylar protrusions forming separated bearing surfaces configured to articulate with the tibial component. In one disclosed embodiment the posterior portion of the tibial post has a concave surface in the sagittal plane and a convex surface in the transverse plane, and the femoral component includes an intercondylar femoral cam mechanism configured to articulate with the posterior surface of the tibial post. The femoral cam mechanism may include an intercondylar bridging structure with distinct bars or interconnected structural elements providing convex and concave distal surfaces in the sagittal plane, and a concave surface in the transverse plane to facilitate rotation of the femoral component relative to the tibial component in the transverse plane.

2 Claims, 6 Drawing Sheets

(56) References Cited

U.S. PATENT DOCUMENTS

| | | |
|---|---|---|
| 3,855,638 A | 12/1974 | Pilliar |
| 3,869,731 A | 3/1975 | Waugh et al. |
| 4,081,866 A | 4/1978 | Upshaw et al. |
| 4,156,943 A | 6/1979 | Collier |
| 4,206,516 A | 6/1980 | Pilliar |
| 4,209,861 A | 7/1980 | Walker et al. |
| 4,213,209 A | 7/1980 | Insall et al. |
| 4,215,439 A | 8/1980 | Gold et al. |
| 4,249,270 A | 2/1981 | Bahler et al. |
| 4,257,129 A | 3/1981 | Volz |
| 4,262,368 A | 4/1981 | Lacey |
| 4,298,992 A | 11/1981 | Burstein et al. |
| 4,340,978 A | 7/1982 | Buechel et al. |
| 4,470,158 A | 9/1984 | Pappas et al. |
| 4,612,160 A | 9/1986 | Donlevy et al. |
| 4,650,490 A | 3/1987 | Figgie, III |
| 4,673,407 A | 6/1987 | Martin |
| 4,714,474 A | 12/1987 | Brooks, Jr. et al. |
| 4,795,468 A | 1/1989 | Hodorek et al. |
| 4,808,185 A | 2/1989 | Penenberg et al. |
| 4,822,362 A | 4/1989 | Walker et al. |
| 4,838,891 A | 6/1989 | Branemark et al. |
| 4,888,021 A | 12/1989 | Forte et al. |
| 4,892,547 A | 1/1990 | Brown |
| 4,936,847 A | 6/1990 | Manginelli |
| 4,936,853 A | 6/1990 | Fabian et al. |
| 4,938,769 A | 7/1990 | Shaw |
| 4,944,757 A | 7/1990 | Martinez et al. |
| 4,944,760 A | 7/1990 | Kenna |
| 4,950,298 A | 8/1990 | Gustilo et al. |
| 4,959,071 A | 9/1990 | Brown et al. |
| 4,963,152 A | 10/1990 | Hofmann et al. |
| 4,990,163 A | 2/1991 | Ducheyne et al. |
| 5,007,932 A | 4/1991 | Bekki et al. |
| 5,007,933 A | 4/1991 | Sidebotham et al. |
| 5,011,496 A | 4/1991 | Forte et al. |
| 5,019,103 A | 5/1991 | Van Zile et al. |
| 5,037,423 A | 8/1991 | Kenna |
| 5,071,438 A | 12/1991 | Jones et al. |
| 5,080,675 A | 1/1992 | Lawes et al. |
| 5,104,410 A | 4/1992 | Chowdhary |
| 5,108,442 A | 4/1992 | Smith |
| 5,116,375 A | 5/1992 | Hofmann |
| 5,133,758 A | 7/1992 | Hollister |
| 5,133,759 A | 7/1992 | Turner |
| 5,147,405 A | 9/1992 | Van Zile et al. |
| 5,147,406 A | 9/1992 | Houston et al. |
| 5,152,797 A | 10/1992 | Luckman et al. |
| 5,171,283 A | 12/1992 | Pappas et al. |
| 5,201,766 A | 4/1993 | Georgette |
| 5,219,362 A | 6/1993 | Tuke et al. |
| 5,236,461 A | 8/1993 | Forte |
| 5,251,468 A | 10/1993 | Lin et al. |
| 5,258,044 A | 11/1993 | Lee |
| 5,271,737 A | 12/1993 | Baldwin et al. |
| 5,282,861 A | 2/1994 | Kaplan |
| 5,308,556 A | 5/1994 | Bagley |
| 5,309,639 A | 5/1994 | Lee |
| 5,326,361 A | 7/1994 | Hollister |
| 5,330,533 A | 7/1994 | Walker et al. |
| 5,330,534 A | 7/1994 | Herrington et al. |
| 5,344,460 A | 9/1994 | Turanyi et al. |
| 5,344,461 A | 9/1994 | Phlipot |
| 5,344,494 A | 9/1994 | Davidson et al. |
| 5,358,527 A | 10/1994 | Forte |
| 5,368,881 A | 11/1994 | Kelman et al. |
| 5,370,699 A | 12/1994 | Hood et al. |
| 5,387,240 A | 2/1995 | Pottenger et al. |
| 5,395,401 A | 3/1995 | Bahler |
| 5,405,396 A | 4/1995 | Heldreth et al. |
| 5,413,604 A | 5/1995 | Hodge |
| 5,414,049 A | 5/1995 | Sun et al. |
| 5,449,745 A | 9/1995 | Sun et al. |
| 5,458,637 A | 10/1995 | Hayes |
| 5,480,445 A | 1/1996 | Burkinshaw |
| 5,480,446 A | 1/1996 | Goodfellow et al. |
| 5,543,471 A | 8/1996 | Sun et al. |
| 5,549,686 A | 8/1996 | Johnson et al. |
| 5,549,687 A | 8/1996 | Coates et al. |
| D374,078 S | 9/1996 | Johnson et al. |
| 5,554,158 A | 9/1996 | Vinciguerra et al. |
| 5,571,187 A | 11/1996 | Devanathan |
| 5,571,194 A | 11/1996 | Gabriel |
| 5,609,639 A | 3/1997 | Walker |
| 5,609,643 A | 3/1997 | Colleran et al. |
| 5,639,279 A | 6/1997 | Burkinshaw et al. |
| 5,650,485 A | 7/1997 | Sun et al. |
| 5,658,333 A | 8/1997 | Kelman et al. |
| 5,658,342 A | 8/1997 | Draganich et al. |
| 5,658,344 A | 8/1997 | Hurlburt |
| 5,681,354 A | 10/1997 | Eckhoff |
| 5,683,468 A | 11/1997 | Pappas |
| 5,702,458 A | 12/1997 | Burstein et al. |
| 5,702,463 A | 12/1997 | Pothier et al. |
| 5,702,464 A | 12/1997 | Lackey et al. |
| 5,702,466 A | 12/1997 | Pappas et al. |
| 5,728,748 A | 3/1998 | Sun et al. |
| 5,732,469 A | 3/1998 | Hamamoto et al. |
| 5,755,800 A | 5/1998 | O'Neil et al. |
| 5,755,801 A | 5/1998 | Walker et al. |
| 5,755,803 A | 5/1998 | Haines et al. |
| 5,765,095 A | 6/1998 | Flak et al. |
| 5,766,257 A | 6/1998 | Goodman et al. |
| 5,776,201 A | 7/1998 | Colleran et al. |
| 5,800,552 A | 9/1998 | Forte |
| 5,811,543 A | 9/1998 | Hao et al. |
| 5,824,100 A | 10/1998 | Kester et al. |
| 5,824,102 A | 10/1998 | Buscayret |
| 5,824,103 A | 10/1998 | Williams |
| 5,871,543 A | 2/1999 | Hofmann |
| 5,871,545 A | 2/1999 | Goodfellow et al. |
| 5,871,546 A | 2/1999 | Colleran et al. |
| 5,879,392 A | 3/1999 | McMinn et al. |
| 5,879,394 A | 3/1999 | Ashby et al. |
| 5,879,400 A | 3/1999 | Merrill et al. |
| 5,906,644 A | 5/1999 | Powell |
| 5,935,173 A | 8/1999 | Roger et al. |
| 5,951,603 A | 9/1999 | O'Neil et al. |
| 5,957,979 A | 9/1999 | Beckman et al. |
| 5,964,808 A | 10/1999 | Blaha et al. |
| 5,976,147 A | 11/1999 | LaSalle et al. |
| 5,984,969 A | 11/1999 | Matthews et al. |
| 5,989,027 A | 11/1999 | Wagner et al. |
| 5,997,577 A | 12/1999 | Herrington et al. |
| 6,004,351 A | 12/1999 | Tomita et al. |
| 6,005,018 A | 12/1999 | Cicierega et al. |
| 6,010,534 A | 1/2000 | O'Neil et al. |
| 6,013,103 A | 1/2000 | Kaufman et al. |
| 6,017,975 A | 1/2000 | Saum et al. |
| 6,039,764 A | 3/2000 | Pottenger et al. |
| 6,042,780 A | 3/2000 | Huang |
| 6,053,945 A | 4/2000 | O'Neil et al. |
| 6,059,949 A | 5/2000 | Gal-Or et al. |
| 6,068,658 A | 5/2000 | Insall et al. |
| 6,080,195 A | 6/2000 | Colleran et al. |
| 6,090,144 A | 7/2000 | Letot et al. |
| 6,123,728 A | 9/2000 | Brosnahan et al. |
| 6,123,729 A | 9/2000 | Insall et al. |
| 6,123,896 A | 9/2000 | Meeks, III et al. |
| 6,126,692 A | 10/2000 | Robie et al. |
| 6,135,857 A | 10/2000 | Shaw et al. |
| 6,139,581 A | 10/2000 | Engh et al. |
| 6,152,960 A | 11/2000 | Pappas |
| 6,162,254 A | 12/2000 | Timoteo |
| 6,174,934 B1 | 1/2001 | Sun et al. |
| 6,206,926 B1 | 3/2001 | Pappas |
| 6,210,444 B1 | 4/2001 | Webster et al. |
| 6,210,445 B1 | 4/2001 | Zawadzki |
| 6,217,618 B1 | 4/2001 | Hileman |
| 6,228,900 B1 | 5/2001 | Shen et al. |
| 6,238,434 B1 | 5/2001 | Pappas |
| 6,242,507 B1 | 6/2001 | Saum et al. |
| 6,245,276 B1 | 6/2001 | McNulty et al. |
| 6,258,127 B1 | 7/2001 | Schmotzer |

(56) References Cited

U.S. PATENT DOCUMENTS

| | | |
|---|---|---|
| 6,264,697 B1 | 7/2001 | Walker |
| 6,280,476 B1 | 8/2001 | Metzger et al. |
| 6,281,264 B1 | 8/2001 | Salovey et al. |
| 6,299,646 B1 | 10/2001 | Chambat et al. |
| 6,316,158 B1 | 11/2001 | Saum et al. |
| 6,319,283 B1 | 11/2001 | Insall et al. |
| 6,325,828 B1 | 12/2001 | Dennis et al. |
| 6,344,059 B1 | 2/2002 | Krakovits et al. |
| 6,361,564 B1 | 3/2002 | Marceaux et al. |
| 6,372,814 B1 | 4/2002 | Sun et al. |
| 6,379,388 B1 | 4/2002 | Ensign et al. |
| 6,428,577 B1 | 8/2002 | Evans et al. |
| 6,443,991 B1 | 9/2002 | Running |
| 6,475,241 B2 | 11/2002 | Pappas |
| 6,485,519 B2 | 11/2002 | Meyers et al. |
| 6,491,726 B2 | 12/2002 | Pappas |
| 6,494,914 B2 | 12/2002 | Brown et al. |
| 6,503,280 B2 | 1/2003 | Repicci |
| 6,506,215 B1 | 1/2003 | Letot et al. |
| 6,506,216 B1 | 1/2003 | McCue et al. |
| 6,524,522 B2 | 2/2003 | Vaidyanathan et al. |
| 6,540,787 B2 | 4/2003 | Biegun et al. |
| 6,558,426 B1 | 5/2003 | Masini |
| 6,569,202 B2 | 5/2003 | Whiteside |
| 6,582,469 B1 | 6/2003 | Tornier |
| 6,582,470 B1 | 6/2003 | Lee et al. |
| 6,589,283 B1 | 7/2003 | Metzger et al. |
| 6,592,787 B2 | 7/2003 | Pickrell et al. |
| 6,620,198 B2 | 9/2003 | Burstein et al. |
| 6,623,526 B1 | 9/2003 | Lloyd |
| 6,645,251 B2 | 11/2003 | Salehi et al. |
| 6,660,039 B1 | 12/2003 | Evans et al. |
| 6,660,224 B2 | 12/2003 | Lefebvre et al. |
| 6,664,308 B2 | 12/2003 | Sun et al. |
| 6,702,821 B2 | 3/2004 | Bonutti |
| 6,719,800 B2 | 4/2004 | Meyers et al. |
| 6,726,724 B2 | 4/2004 | Repicci |
| 6,730,128 B2 | 5/2004 | Burstein |
| 6,764,516 B2 | 7/2004 | Pappas |
| 6,770,078 B2 | 8/2004 | Bonutti |
| 6,770,099 B2 | 8/2004 | Andriacchi et al. |
| 6,773,461 B2 | 8/2004 | Meyers et al. |
| 6,797,005 B2 | 9/2004 | Pappas |
| 6,818,020 B2 | 11/2004 | Sun et al. |
| 6,846,327 B2 | 1/2005 | Khandkar et al. |
| 6,846,329 B2 | 1/2005 | McMinn |
| 6,849,230 B1 | 2/2005 | Feichtinger |
| 6,852,272 B2 | 2/2005 | Artz et al. |
| 6,869,448 B2 | 3/2005 | Tuke et al. |
| 6,893,388 B2 | 5/2005 | Reising et al. |
| 6,893,467 B1 | 5/2005 | Bercovy |
| 6,916,340 B2 | 7/2005 | Metzger et al. |
| 6,923,832 B1 | 8/2005 | Sharkey et al. |
| 6,926,738 B2 | 8/2005 | Wyss |
| 6,942,670 B2 | 9/2005 | Heldreth et al. |
| 6,972,039 B2 | 12/2005 | Metzger et al. |
| 6,986,791 B1 | 1/2006 | Metzger |
| 7,025,788 B2 | 4/2006 | Metzger et al. |
| 7,048,741 B2 | 5/2006 | Swanson |
| 7,066,963 B2 | 6/2006 | Naegerl |
| 7,070,622 B1 | 7/2006 | Brown et al. |
| 7,081,137 B1 | 7/2006 | Servidio |
| 7,094,259 B2 | 8/2006 | Tarabichi |
| 7,101,401 B2 | 9/2006 | Brack |
| 7,104,996 B2 | 9/2006 | Bonutti |
| 7,105,027 B2 | 9/2006 | Lipman et al. |
| 7,147,819 B2 | 12/2006 | Bram et al. |
| 7,160,330 B2 | 1/2007 | Axelson, Jr. et al. |
| 7,175,665 B2 | 2/2007 | German et al. |
| 7,255,715 B2 | 8/2007 | Metzger |
| 7,261,740 B2 | 8/2007 | Tuttle et al. |
| 7,297,164 B2 | 11/2007 | Johnson et al. |
| 7,326,252 B2 | 2/2008 | Otto et al. |
| 7,341,602 B2 | 3/2008 | Fell et al. |
| 7,344,460 B2 | 3/2008 | Gait |
| 7,357,817 B2 | 4/2008 | D'Alessio, II |
| 7,422,605 B2 | 9/2008 | Burstein et al. |
| 7,510,557 B1 | 3/2009 | Bonutti |
| 7,527,650 B2 | 5/2009 | Johnson et al. |
| 7,572,292 B2 | 8/2009 | Crabtree et al. |
| 7,578,850 B2 | 8/2009 | Kuczynski et al. |
| 7,608,079 B1 | 10/2009 | Blackwell et al. |
| 7,611,519 B2 | 11/2009 | Lefevre et al. |
| 7,615,054 B1 | 11/2009 | Bonutti |
| 7,618,462 B2 | 11/2009 | Ek |
| 7,628,818 B2 | 12/2009 | Hazebrouck et al. |
| 7,635,390 B1 | 12/2009 | Bonutti |
| 7,658,767 B2 | 2/2010 | Wyss |
| 7,678,151 B2 | 3/2010 | Ek |
| 7,678,152 B2 | 3/2010 | Suguro et al. |
| 7,708,740 B1 | 5/2010 | Bonutti |
| 7,708,741 B1 | 5/2010 | Bonutti |
| 7,740,662 B2 | 6/2010 | Barnett et al. |
| 7,749,229 B1 | 7/2010 | Bonutti |
| 7,753,960 B2 | 7/2010 | Cipolletti et al. |
| 7,771,484 B2 | 8/2010 | Campbell |
| 7,776,044 B2 | 8/2010 | Pendleton et al. |
| 7,806,896 B1 | 10/2010 | Bonutti |
| 7,806,897 B1 | 10/2010 | Bonutti |
| 7,837,736 B2 | 11/2010 | Bonutti |
| 7,842,093 B2 | 11/2010 | Peters et al. |
| 7,875,081 B2 | 1/2011 | Lipman et al. |
| 7,922,771 B2 | 4/2011 | Otto et al. |
| 2003/0009232 A1 | 1/2003 | Metzger et al. |
| 2003/0035747 A1 | 2/2003 | Anderson et al. |
| 2003/0044301 A1 | 3/2003 | Lefebvre et al. |
| 2003/0075013 A1 | 4/2003 | Grohowski |
| 2003/0139817 A1 | 7/2003 | Tuke et al. |
| 2003/0153981 A1 | 8/2003 | Wang et al. |
| 2003/0171820 A1 | 9/2003 | Wilshaw et al. |
| 2003/0199985 A1 | 10/2003 | Masini |
| 2003/0212161 A1 | 11/2003 | McKellop et al. |
| 2003/0225456 A1 | 12/2003 | Ek |
| 2004/0015770 A1 | 1/2004 | Kimoto |
| 2004/0039450 A1 | 2/2004 | Griner et al. |
| 2004/0167633 A1 | 8/2004 | Wen et al. |
| 2004/0186583 A1 | 9/2004 | Keller |
| 2004/0215345 A1 | 10/2004 | Perrone et al. |
| 2004/0243244 A1 | 12/2004 | Otto et al. |
| 2004/0243245 A1 | 12/2004 | Plumet et al. |
| 2005/0021147 A1 | 1/2005 | Tarabichi |
| 2005/0055102 A1 | 3/2005 | Tornier et al. |
| 2005/0059750 A1 | 3/2005 | Sun et al. |
| 2005/0069629 A1 | 3/2005 | Becker et al. |
| 2005/0096747 A1 | 5/2005 | Tuttle et al. |
| 2005/0100578 A1 | 5/2005 | Schmid et al. |
| 2005/0123672 A1 | 6/2005 | Justin et al. |
| 2005/0143832 A1 | 6/2005 | Carson |
| 2005/0154472 A1 | 7/2005 | Afriat |
| 2005/0203631 A1 | 9/2005 | Daniels et al. |
| 2005/0209701 A1 | 9/2005 | Suguro et al. |
| 2005/0209702 A1 | 9/2005 | Todd et al. |
| 2005/0249625 A1 | 11/2005 | Bram et al. |
| 2006/0002810 A1 | 1/2006 | Grohowski |
| 2006/0015185 A1 | 1/2006 | Chambat et al. |
| 2006/0036329 A1 | 2/2006 | Webster et al. |
| 2006/0052875 A1 | 3/2006 | Bernero et al. |
| 2006/0100714 A1 | 5/2006 | Ensign |
| 2006/0178749 A1 | 8/2006 | Pendleton et al. |
| 2006/0195195 A1 | 8/2006 | Burstein et al. |
| 2006/0228247 A1 | 10/2006 | Grohowski |
| 2006/0231402 A1 | 10/2006 | Clasen et al. |
| 2006/0241781 A1 | 10/2006 | Brown et al. |
| 2006/0257358 A1 | 11/2006 | Wen et al. |
| 2006/0271191 A1 | 11/2006 | Hermansson |
| 2006/0289388 A1 | 12/2006 | Yang et al. |
| 2007/0061014 A1 | 3/2007 | Naegerl |
| 2007/0073409 A1 | 3/2007 | Cooney et al. |
| 2007/0078521 A1 | 4/2007 | Overholser et al. |
| 2007/0100463 A1 | 5/2007 | Aram et al. |
| 2007/0129809 A1 | 6/2007 | Meridew et al. |
| 2007/0135926 A1 | 6/2007 | Walker |
| 2007/0173948 A1 | 7/2007 | Meridew et al. |
| 2007/0196230 A1 | 8/2007 | Hamman et al. |

(56) References Cited

U.S. PATENT DOCUMENTS

| | | |
|---|---|---|
| 2007/0203582 A1 | 8/2007 | Campbell |
| 2007/0219639 A1 | 9/2007 | Otto et al. |
| 2007/0293647 A1 | 12/2007 | McKellop et al. |
| 2008/0004708 A1 | 1/2008 | Wyss |
| 2008/0021566 A1 | 1/2008 | Peters et al. |
| 2008/0091272 A1 | 4/2008 | Aram et al. |
| 2008/0097616 A1 | 4/2008 | Meyers et al. |
| 2008/0114462 A1 | 5/2008 | Guidera et al. |
| 2008/0114464 A1 | 5/2008 | Barnett et al. |
| 2008/0119940 A1 | 5/2008 | Otto et al. |
| 2008/0161927 A1 | 7/2008 | Savage et al. |
| 2008/0195108 A1 | 8/2008 | Bhatnagar et al. |
| 2008/0199720 A1 | 8/2008 | Liu |
| 2008/0206297 A1 | 8/2008 | Roeder et al. |
| 2008/0269596 A1 | 10/2008 | Revie et al. |
| 2009/0043396 A1 | 2/2009 | Komistek |
| 2009/0048680 A1 | 2/2009 | Naegerl |
| 2009/0082873 A1 | 3/2009 | Hazebrouck et al. |
| 2009/0084491 A1 | 4/2009 | Uthgenannt et al. |
| 2009/0088859 A1 | 4/2009 | Hazebrouck et al. |
| 2009/0125114 A1 | 5/2009 | May et al. |
| 2009/0192610 A1 | 7/2009 | Case et al. |
| 2009/0265012 A1 | 10/2009 | Engh et al. |
| 2009/0265013 A1 | 10/2009 | Mandell |
| 2009/0292365 A1 | 11/2009 | Smith et al. |
| 2009/0295035 A1 | 12/2009 | Evans |
| 2009/0306785 A1 | 12/2009 | Farrar et al. |
| 2009/0319047 A1 | 12/2009 | Walker |
| 2009/0326663 A1 | 12/2009 | Dun |
| 2009/0326664 A1 | 12/2009 | Wagner et al. |
| 2009/0326665 A1 | 12/2009 | Wyss et al. |
| 2009/0326666 A1 | 12/2009 | Wyss et al. |
| 2009/0326667 A1 | 12/2009 | Williams et al. |
| 2009/0326674 A1 | 12/2009 | Liu et al. |
| 2010/0016979 A1 | 1/2010 | Wyss et al. |
| 2010/0036499 A1 | 2/2010 | Pinskerova |
| 2010/0036500 A1 | 2/2010 | Heldreth et al. |
| 2010/0042224 A1 | 2/2010 | Otto et al. |
| 2010/0042225 A1 | 2/2010 | Shur |
| 2010/0063594 A1 | 3/2010 | Hazebrouck et al. |
| 2010/0070045 A1 | 3/2010 | Ek |
| 2010/0076563 A1 | 3/2010 | Otto et al. |
| 2010/0076564 A1 | 3/2010 | Schilling et al. |
| 2010/0094429 A1 | 4/2010 | Otto |
| 2010/0098574 A1 | 4/2010 | Liu et al. |
| 2010/0100189 A1 | 4/2010 | Metzger |
| 2010/0100190 A1 | 4/2010 | May et al. |
| 2010/0100191 A1 | 4/2010 | May et al. |
| 2010/0125337 A1 | 5/2010 | Grecco et al. |
| 2010/0161067 A1 | 6/2010 | Saleh et al. |
| 2010/0191341 A1 | 7/2010 | Byrd |
| 2010/0222890 A1 | 9/2010 | Barnett et al. |
| 2010/0286788 A1 | 11/2010 | Komistek |
| 2010/0292804 A1 | 11/2010 | Samuelson |
| 2010/0305710 A1 | 12/2010 | Metzger et al. |
| 2010/0312350 A1 | 12/2010 | Bonutti |
| 2011/0029090 A1 | 2/2011 | Zannis et al. |
| 2011/0029092 A1 | 2/2011 | Deruntz et al. |
| 2011/0035017 A1 | 2/2011 | Deffenbaugh et al. |
| 2011/0035018 A1 | 2/2011 | Deffenbaugh et al. |
| 2011/0106268 A1 | 5/2011 | Deffenbaugh et al. |
| 2011/0118847 A1 | 5/2011 | Lipman et al. |
| 2011/0125280 A1 | 5/2011 | Otto et al. |
| 2011/0153026 A1 | 6/2011 | Heggendorn et al. |

FOREIGN PATENT DOCUMENTS

| | | |
|---|---|---|
| EP | 495340 A1 | 7/1992 |
| EP | 510178 A1 | 10/1992 |
| EP | 634155 A2 | 1/1995 |
| EP | 636352 A2 | 2/1995 |
| EP | 732091 A2 | 9/1996 |
| EP | 883388 A1 | 12/1998 |
| EP | 634156 B1 | 5/1999 |
| EP | 1129676 A1 | 9/2001 |
| EP | 732092 B1 | 2/2002 |
| EP | 1196118 A1 | 4/2002 |
| EP | 765645 B1 | 8/2003 |
| EP | 1374805 A2 | 1/2004 |
| EP | 1421918 A1 | 5/2004 |
| EP | 1440675 A1 | 7/2004 |
| EP | 1470801 A1 | 10/2004 |
| EP | 1518521 A2 | 3/2005 |
| EP | 1226799 B1 | 5/2005 |
| EP | 1591082 A2 | 11/2005 |
| EP | 1779812 A1 | 5/2007 |
| EP | 1923079 A1 | 5/2008 |
| FR | 2417971 A1 | 9/1979 |
| FR | 2621243 A1 | 4/1989 |
| FR | 2653992 A1 | 5/1991 |
| FR | 2780636 A1 | 1/2000 |
| FR | 2787012 A1 | 6/2000 |
| FR | 2809302 A1 | 11/2001 |
| FR | 2835178 A1 | 8/2003 |
| GB | 1065354 A | 4/1967 |
| GB | 2293109 A | 3/1996 |
| GB | 2335145 A | 9/1999 |
| JP | 62205201 A | 9/1987 |
| JP | 8500992 T | 2/1996 |
| JP | 2004167255 A | 6/2004 |
| WO | WO-7900739 A1 | 10/1979 |
| WO | WO-8906947 A1 | 8/1989 |
| WO | WO-9014806 A1 | 12/1990 |
| WO | WO-9601725 A1 | 1/1996 |
| WO | WO-9623458 A1 | 8/1996 |
| WO | WO-9624311 A1 | 8/1996 |
| WO | WO-9624312 A1 | 8/1996 |
| WO | WO-9846171 A1 | 10/1998 |
| WO | WO-9927872 A1 | 6/1999 |
| WO | WO-9966864 A1 | 12/1999 |
| WO | WO-0209624 A1 | 2/2002 |
| WO | WO-03039609 A1 | 5/2003 |
| WO | WO-03101647 A2 | 12/2003 |
| WO | WO-2004058108 A1 | 7/2004 |
| WO | WO-2004069104 A1 | 8/2004 |
| WO | WO-2005009489 A2 | 2/2005 |
| WO | WO-2005009729 A2 | 2/2005 |
| WO | WO-2005072657 A1 | 8/2005 |
| WO | WO-2005087125 A2 | 9/2005 |
| WO | WO-2006014294 A1 | 2/2006 |
| WO | WO-2006130350 A2 | 12/2006 |
| WO | WO-2007106172 A1 | 9/2007 |
| WO | WO-2007108804 A1 | 9/2007 |
| WO | WO-2007119173 A2 | 10/2007 |
| WO | WO-2008100784 A2 | 8/2008 |
| WO | WO-2009046212 A2 | 4/2009 |
| WO | WO-2009128943 A2 | 10/2009 |

OTHER PUBLICATIONS

Asano et al. "In Vivo Three-Dimensional Knee Kinematics Using a Biplanar Image-Matching Technique," Clin Orthop Rel Res, 388: 157-166, 2001, (10 pages).

Clary et al., "Kinematics of Posterior Stabilized and Cruciate Retaining Knee Implants During an in Vitro Deep Knee Bend," 54th Annual Meeting of the Orthopaedic Research Society, Poster No. 1983, Mar. 2008.

Dennis et al., "In vivo anteroposterior femorotibial translation of total knee arthroplasty: a multicenter analysis," Clin Orthop Rel Res, 356: 47-57, 1998.

European Search Report for European Patent Application No. 09164235.5, Dec. 22, 2009, 6 pgs.

European Search Report for European Patent Application No. 09164168.8, Jan. 4, 2010, 6 pgs.

"Vanguard Complete Knee System," Biomet, available at: http://www.biomet.com/patients/vanguard_complete.cfm, downloaded on Feb. 2009, (3 pages).

"NexGen Complete Knee Solution Cruciate Retaining Knee (CR)," Zimmer, available at: http://zimmer.com.au/ctl?template=PC&op=global&action=&template=PC&id=356, downloaded on Feb. 18, 2009, (1 page).

(56) References Cited

OTHER PUBLICATIONS

P. Johal et al, "Tibio-femoral movement in the living knee. A study of weight bearing and non-weight bearing knee kinematics using 'interventional' MRI," Journal of Biomechanics, vol. 38, Issue 2, Feb. 2005, pp. 269-276, (8 pages).
European Search Report for European Patent Application No. 09164160.5, Jan. 4, 2010, 4 pgs.
European Search Report for European Patent Application No. 09164228.0, Feb. 2, 2010, 6 pgs.
Kessler et al., "Sagittal curvature of total knee replacements predicts in vivo kinematics," Clinical Biomechanics 22(1): 52-58, 2007.
Wang et al., "Biomechanical differences exhibited during sit-to-stand between total knee arthroplasty designs of varying radii," J Arthroplasty 21(8): 1193-9, 2006.
Saari et al., "The effect of tibial insert design on rising from a chair; motion analysis after total knee replacement," Clin Biomech 19(9): 951-6, 2004.
Ranawat, "Design may be counterproductive for optimizing flexion after TKR," Clin Orthop Rel Res 416: 174-6, 2003.
D'Lima et al., "Quadriceps moment arm and quadriceps forces after total knee arthroplasty," Clin Orthop Rel Res 392:213-20, 2001.
Uvehammer et al., "In vivo kinematics of total knee anthroplasty: concave versus posterior-stabilised tibial joint surface," The Journal of Bone & Joint Surgery 82B (4): 499-505, 2000.
Wang et al., "A biomechanical comparison between the single-axis and multi-axis total knee arthroplasty systems for stand-to-sit movement," Clin Biomech 20(4): 428-33, 2005.
Yoshiya et al., "In Vivo Kinematic Comparison of Posterior Cruciate-Retaining and Posterior Stabilized Total Knee Arthroplasties Under Passive and Weight-bearing Conditions," J. Arthroplasty, vol. 20, No. 6, 2005, 7 pgs.
Bertin et al., "In Vivo Determination of Posterior Femoral Rollback for Subjects Having a NexGen Posterior Cruciate-Retaining Total Knee Arthroplasty," J. Arthroplasty, vol. 17, No. 8, 2002, 9 pgs.
Suggs et al., "Three-Dimensional Tibiofemoral Articular Contact Kinematics of a Cruciate-Retaining Total Knee Arthroplasty," JBJS-Am, vol. 88, No. 2, 2006, 9 pgs.
Dennis et al., "In Vivo Determination of Normal and Anterior Cruciate Ligament-Deficient Knee Kinematics," J. Biomechanics, 38, 241-253, 2005, 13 pgs.
Li et al., "Anterior Cruciate Ligament Deficiency Alters the In Vivo Motion of the Tibiofemoral Cartilage Contact Points in Both Anteroposterior and Mediolateral Directions," JBJS-Am, vol. 88, No. 8, Aug. 2006, 10 pgs.
Ries, "Effect of ACL Sacrifice, Retention, or Substitution on K After TKA," http://www.orthosupersite.com/view.asp?rID=23134, Aug. 2007, 5 pgs.
European search report; European Application No. 10174439.9; Dec. 20, 2010; 4 pages.
Zimmer, Trabecular Metal Monoblock Tibial Components, An Optimal Combination of Material and Design, www.zimmer.com, 2009, 3 pages.
Zimmer Nexgen Trabecular Metal Tibial Tray, The Best Thing Next to Bone, 97-5954-001-00, 2007, 4 pages.
European Search Report for European Patent Application No. 08164944.4, Mar. 16, 2009, 12 pgs.
Signus Medizintechnik, "Peek-Optima®, The Polymer for Implants, Technical Information for the Medical Profession", 7 pages. 1991.
The Effects of Conformity and Load in Total Knee Replacement, Kuster, et al, Clinical Orthopaedics and Related Research No. 375, Jun. 2000.
Shaw et al., "The Longitudinal Axis of the Knee and the Role of the Cruciate Ligaments in Controlling Transverse Rotation", J.Bone Joint Surg. Am. 1974:56:1603-1609, 8 pages.
Kurosawa, et al., "Geometry and Motion of the Knee for Implant and Orthotic Design", The Journal of Biomechanics 18 (1985), pp. 487-499, 12 pages.

Barnes, C.L., et al., "Kneeling is Safe for Patients Implanted With Medial-Pivot Total Knee Arthroplasty Designs, Journal of Arthroplasty", vol. 00, No. 0 2010, 1-6, 6 pages.
Blaha, et al., "Kinematics of the Human Knee Using an Open Chain Cadaver Model", Clinical Orthopaedics and Related Research, vol. 410 (2003); 25-34, 10 pages.
Dennis, et al., "A Multicenter Analysis of Axial Femorotibial Rotation After Total Knee Arthroplasty", Clinical Orthopaedics 428 (2004); 180-189, 10 pages.
Fan, Cheng-Yu, et al., "Primitive Results After Medial-Pivot Knee Arthroplasties: A Minimum 5-Year Follow-Up Study", The Journal of Arthroplasty, vol. 25, No. 3 2010, 492-496, 5 pages.
Freeman, M.A.R., et al., "The Movement of the Normal Tibio-Femoral Joint", The Journal of Biomechanics 38 (2005) (2), pp. 197-208, 12 pgs.
Fuller, et al., "A Comparison of Lower-Extremity Skeletal Kinematics Measured Using Skin and Pin-Mounted Markers", Human Movement Science 16 (1997) 219-242, 24 pages.
Karachalios, et al., "A Mid-Term Clinical Outcome Study of the Advance Medial Pivot Knee Arthroplasty", www.sciencedirect.com, The Knee 16 (2009); 484-488, 5 pages.
Komistek, et al., "In Vivo Flouroscopic Analysis of the Normal Human Knee", Clinical Orthopaedics 410 (2003): 69-81, 13 pages.
Komistek, et al., "In Vivo Polyethylene Bearing Mobility is Maintained in Posterior Stabilized Total Knee Arthroplasty", Clinical Orthopaedics 428 (2004): 207-213, 7 pages.
Koo, et al., "The Knee Joint Center of Rotation is Predominantly on the Lateral Side During Normal Walking", Journal of Biomechanics, vol. 41 (2008): 1269-1273, 5 pages.
Mannan, et al., "The Medial Rotation Total Knee Replacement: A Clinical and Radiological Review at a Mean Follow-Up of Six Years", The Journal of Bone and Joint Surgery, vol. 91-B, No. 6 (Jun. 2009): 750-756, 7 pages.
Moonot, et al., "Correlation Between the Oxford Knee and American Knee Society Scores at Mid-Term Follow-Up", The Journal of Knee Surgery, vol. 22, No. 3 (Jul. 2009), 226-230, 5 pages.
Murphy, Michael Charles, "Geometry and the Kinematics of the Normal Human Knee", Submitted to Massachusetts Institute of Technology (1990), 379 pages.
Nakagawa, et al., "Tibiofemoral Movement 3: Full Flexion in the Living Knee Studied by MRI", J.Bone Joint Surg. AM, vol. 82-B, No. 8 (2000). 1199-1200, 2 pages.
Omori, et al., "The Effect of Geometry of the Tibial Polyethylene Insert on the Tibiofemoral Contact Kinematics in Advance Medial Pivot Total Knee Arthroplasty", The Journal of Orthopaedic Science (2009), 14: 754-760, 7 pages.
Shakespeare, et al., "Flexion After Total Knee Replacement. A Comparison Between the Medial Pivot Knee and a Posterior Stabilised Implant", www.sciencedirect.com, The Knee 13 (2006): 371-373, 3 pages.
Walker, et al., "Motion of a Mobile Bearing Knee Allowing Translation and Rotation", Journal of Arthroplasty 17 (2002): 11-19, 9 pages.
European Patent Office, Search Report for App. No. 09164479.9, mailed Nov. 4, 2009, 6 pages.
2nd Int'l Johnson-Elloy Knee Meeting, Mar. 1987, 9 pages.
Operative Technique, Johnson Elloy Knee System, Chas F. Thackray, Ltd., 1988, 34 pgs.
Five to Eight Year Results of the Johnson/Elloy (Accord) Total Knee Arthroplasty, Johnson et al, The Journal of Arthroplasty, vol. 8, No. 1, Feb. 1993, 6 pages.
Factors Affecting the Range of Movement of Total Knee Arthroplasty, Harvey et al, The Journal of Bone and Joint Surgery, vol. 75-B, No. 6, Nov. 1993, 6 pages.
Advice Notice (NI) Mar. 2000, Defect & Investigation Centre, Mar. 13, 2000, 3 pages.
The Johnson-Elloy (Accord) Total Knee Replacement, Norton et al, The Journal of Bone and Joint Surgery (BR), vol. 84B, No. 6, Aug. 2002, 4 pages.
Midvastus Approach in Total Knee Arthroplasty, A Description and a Cadaveric Study Determining the Distance of the Popliteal Artery From the Patellar Margin of the Incision, Cooper et al., The Journal of Arthroplasty, vol. 14, No. 4, 1999, 4 pages.

(56) References Cited

OTHER PUBLICATIONS

Biomet, Vanguard Mono-Lock Tibial System, Patented Convertible Tibial Bearing Technology, 2009, 2 pages.
Carl Zeiss, Zeiss Surfcomm 5000—"Contour and Surface Measuring Machines", 2005, 16 pages.
DePuy Inc., "AMK Total Knee System Product Brochure", 1996, 8 pages.
DePuy Knees International, "Sigma CR Porocoat®," 1 page. 2007.
DePuy Orthopaedics, Inc., "AMK Total Knee System Legent II Surgical Technique", 1998, 30 pages.
DePuy Orthopaedics, Inc., "Sigma Fixed Bearing Knees—Function with Wear Resistance", 2010, 0612-65-508 (Rev. 1) 20 pages.
DePuy Pfc Sigma Rp, "PFC Sigma Knee System with Rotating Platform Technical Monograph", 1999, 0611-29-050 (Rev. 3), 70 pages.
Effects of Coronal Plane Conformity on Tibial Loading in TKA: A Comparison of AGC Flat Versus Conforming Articulations, Berend, et al, Orthopaedic Surgery, Surgical Technology International, XVIII, 6 pages, 2009.
European Search Report for European Patent Application No. 09164245.4, Oct. 15, 2009, 5 pgs.
European Search Report for European Patent Application No. 08253140.1, Dec. 23, 2008, 7 pgs.
European Search Report for European Patent Application No. 11150648.1, Apr. 7, 2011, 4 pages.
European Search Report for European Patent Application No. 06739287.8, Mar. 16, 2010, 3 pages.
European Search Report for European Patent Application No. 09164478.1, Oct. 20, 2009, 6 pages.
European Search Report for European Patent Application No. 09164478.1, Apr. 28, 2010, 12 pages.
European Search Report for European Patent Application No. 10162138.1, Aug. 30, 2010, 7 pages.
Japanese Search Report for Japanese Patent Application No. 2009-501393, Oct. 26, 2010, 5 pages.
Procedure, References Guide for Use with P.F.C. Sigma Knee Systems, 1998, 8 pages.
S.I. Bin, T. S. Nam, "Early results of high-flex total knee arthroplasty: comparison study at 1 year after surgery," Knee Surg. Sports Traumatol Arthrosc (2007) 15:350-355, Oct. 2006.
R. E. Jones, "High-Flexion Rotating-Platform Knees: Rationale, Design and Patient Selection," Orthopedics, vol. 29, No. 9, Sep. 2006.
G. Li, E. Most, P. Sultan, S. Schule, S. Zayontz, S. Park, H. Rubash, "Knee Kinematics with a High-Flexion Posterior Stabilized Total Knee Prosthesis: An In Vitro Robotic Experimental Investigation," Journal of Bone and Joint Surgery, vol. 86, No. 8, Aug. 2004.
J. Argenson, R. Komistek, M. Mahfouz, S. Walker, J. Aubaniac, D. Dennis, "A High Flexion Total Knee Arthroplasty Design Replicates Healthy Knee Motion," Clinical Orthopaedics and Related Research, No. 428, pp. 174-179.
PubMed Abstracts, downloaded Jul. 18, 2007 (www.pubmed.gov).

* cited by examiner

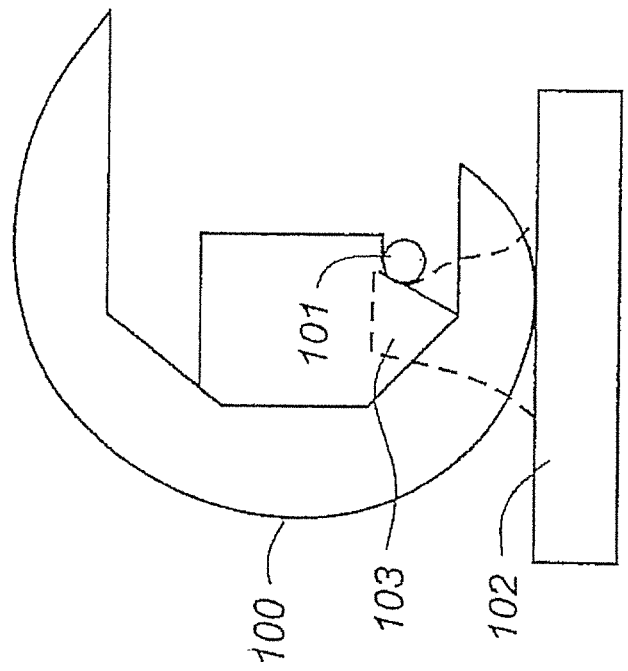
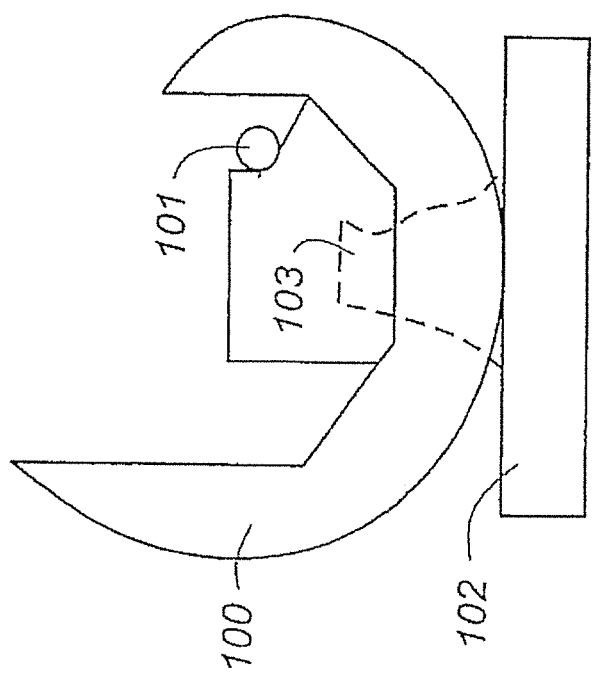
Fig - 1A
(PRIOR ART)
Fig - 1B
(PRIOR ART)

MULTIPLE-CAM, POSTERIOR-STABILIZED KNEE PROSTHESIS

REFERENCE TO RELATED APPLICATIONS

This application is a continuation of U.S. patent application Ser. No. 12/337,280, filed Dec. 17, 2008, now U.S. Pat. No. 8,721,730, which is a continuation of U.S. patent application Ser. No. 10/430,548, filed May 6, 2003, now U.S. Pat. No. 8,273,132, which is a divisional of U.S. patent application Ser. No. 09/724,100, filed Nov. 28, 2000, now U.S. Pat. No. 6,558,426, the content of all of which are incorporated herein in their entirety by reference.

FIELD OF THE INVENTION

This invention relates generally to orthopedic surgery and, in particular, to a posterior stabilized knee prosthesis.

BACKGROUND OF THE INVENTION

In total knee-replacement (TKR) surgery, there are four broad classes of implants used for resurfacing of the distal femur. In one configuration, the posterior cruciate ligament is retained. In another design the ligament is sacrificed, relying on the articular geometry to provide stability. The third type of device is constrained, in the sense that an actual linkage is used between the femoral and tibial components. According to a fourth arrangement, the posterior cruciate is replaced with a cam on the femoral component and a post on the tibial component.

Many patents have been issued in relation to these design configurations, including the cam-and-post design configuration. Some of the earlier patents in this area include U.S. Pat. No. 4,213,209 to Insall et al; U.S. Pat. No. 4,298,992 to Burstein et al.

Other patents include U.S. Pat. No. 4,888,021 to Forte et al., which teaches a cam-and-post mechanism as well as a linking mechanism. Essentially, each component includes a varying surface and a cam member, so that both the tibial and the femoral component have separate and distinct cams that cooperate with a single tibial post.

U.S. Pat. No. 5,824,100 to Kester et al. discloses a cam/post type of arrangement with a unique type of cam and box enclosure. A portion of the box enclosure is intended to prevent hyperextension and posterior translation. As noted in particular in FIGS. 3 and 4 of the '100 patent, a large space exists between the cam 110 and the post 100 which permits a translation to occur prior to engagement of the cam left of post.

U.S. Pat. No. 5,997,577 to Herrington et al. provides a cam on the femur with a geometry meant to contact the post through a large range of motion. This design attempts to provide the function of multiple cams by providing an area that acts as a separate bearing surface. As such, the cam effectively moves through a range of motion while contacting the post. Depending on the articular geometry which differs than the geometry of the cam post mechanism, this could lead to a variety of problems as well as significantly constrained motion, either between the cam and the post or between the two articulating surfaces.

U.S. Pat. No. 5,658,342 to Draganich et al. describes a cam member with including a bearing surface at complimenting an articulating surface. As in other previous designs, this represents a complex cam geometry meant to capture the post in certain degrees of the range of motion.

U.S. Pat. No. 5,147,405 to Van Zyle et al. Discloses a femoral component with two distinct cam structures, one located at point 44, the other located at 46 in the drawings. The cam member 44 is meant to contact the anterior surface of the post 24 to prevent hyperextension, while cam surface 46 is a posterior located cam meant to have contact throughout the range of flexion. As noted in FIG. 6A of the '405 patent, there is a space between the cam and the post when the knee is in extension, necessitating anterior translation of the femur on the tibia prior to contacting the posterior cam.

Many other patents directed to knee-replacement surgery include cam-and-post mechanisms. But in all cases, either the full range of joint motion is precluded, or translation is allowed to occur which could lead to premature wear. FIG. 1 is a drawing which illustrates a typical prior-art cam-and-post mechanism. Item 102 is a tibial insert or tibial component having a post 103 protruding into a box-like recess of the femoral component 100. FIG. 1A shows the system in extension, whereas FIG. 1B shows the system in flexion. In FIG. 1A, a femoral component 100 includes a cam 101 which has not yet engaged with a post 103.

In FIG. 1B, following a considerable amount of flexion, the cam 101 finally engages with the post 103. Until engagement occurs, however, the component 100 may be permitted to slide relative to the tibial insert. The need remains, therefore, for an improved distal femoral prosthesis having multiple distinct cams contacting a post on its posterior surface to provide more normal range of motion for cruciate substituting knee replacement.

SUMMARY OF THE INVENTION

The present invention resides in a distal femoral knee-replacement component configured for use in a cruciate-substituting situation involving a tibial component having a bearing surface and a superior post with a posterior aspect. As with existing configurations, the component is comprised of a body having a pair of medial and lateral condylar protrusions and an intercondylar region therebetween dimensioned to receive the tibial post. In contrast to prior-art devices, however, the inventive component provides additional points of cam action to facilitate a more normal range of knee motion.

In the preferred embodiment, the invention facilitates a more normal rollback while inhibiting initial translation which could lead to increased wear and sub-optimal patella femoral mechanics. To accomplish this goal, the inventive component includes a distinct point of cam action to prevent early translation at the initiation of flexion, and a distinct point of cam action to prevent a dislocation of the femoral component over the tibial post which is known to occur in cruciate-substituting designs. According to the invention, these points of cam action may be used separately or in combination.

In the preferred embodiment, the component includes three distinct points of cam action. The first is preferably located substantially where existing cams are found, namely, at a point spaced apart a slight distance posteriorly relative to the post in full extension. According to the invention, however, a second point of cam action is located immediately adjacent the posterior aspect of the superior post to minimize and, ideally, prevent anterior translation at the initiation of flexion. The third point of cam action is preferably located more posteriorly to allow enhanced flexion without a dislocation of the knee.

In terms of structure, the points of cam action may be implemented using any member or combination of elements operative to provide distinct stages of cooperation with the posterior aspect of the superior post. For example, transverse bars may be used which bridge, or partially bridge, the intercondylar space. The members or elements need not be straight across, but may instead be curved, with the post being curved to allow for a rotation, if so desired. The cam structures according to the invention may also be connected to one another forming points of contact as opposed to complete transverse elements such as distinct bars.

BRIEF DESCRIPTION OF THE FIGURES

FIG. 1A is a drawing which illustrates a prior-art cam-and-post mechanism in extension;

FIG. 1B is a drawing which illustrates the prior-art cam-and-post mechanism of FIG. 1B in flexion;

DETAILED DESCRIPTION OF THE INVENTION

Figure 2A:
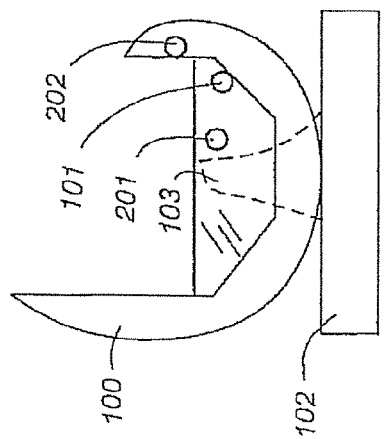
FIG. 2A illustrates a preferred embodiment of the invention in extension.
Figure 2B:
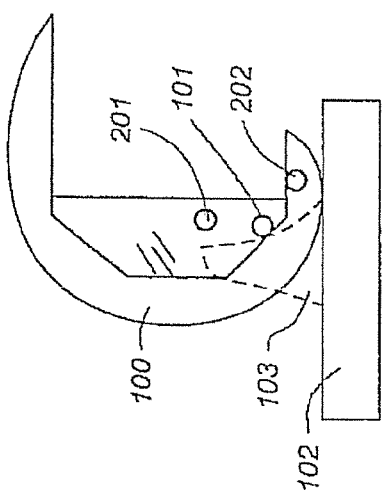
FIG. 2B shows the system of FIG. 2A at 90 degrees flexion.
Figure 2C:
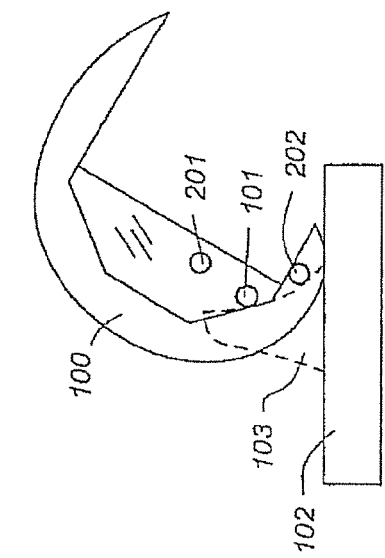
FIG. 2C illustrates the system of FIG. 2A in flexion at 120 degrees or more.

FIGS. 2A through 2C illustrate one embodiment of the invention. FIG. 2A shows the configuration in extension, FIG. 2B shows the system at 90 degrees flexion, and FIG. 2C illustrates flexion of 120 degrees or more. In addition to a conventionally placed cam at 101, two additional points of cam action are preferably provided. In particular, a feature at 201 acts to prevent translation from extension into the initiation of the flexion. Feature 201 preferably disengages as conventional cam 101 is engaged. As the knee follows through a range of motion to 90° of flexion, and beyond, cam 101 disengages and feature 202 engages, if necessary, to prevent dislocation of the component.

Figure 2D:
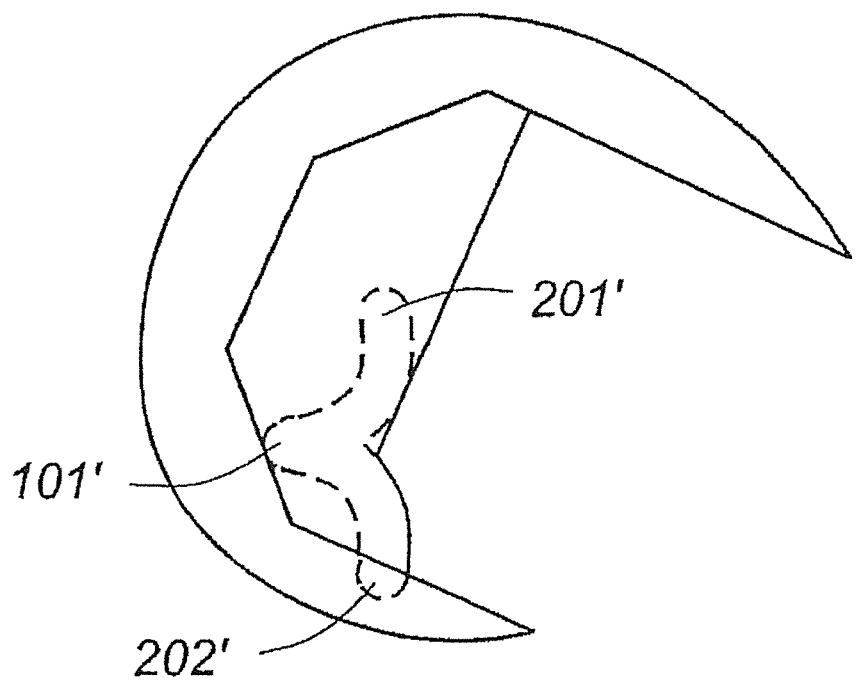
FIG. 2D illustrates the alternative use of interconnected cams with physically separate contact points.
Figure 2E:
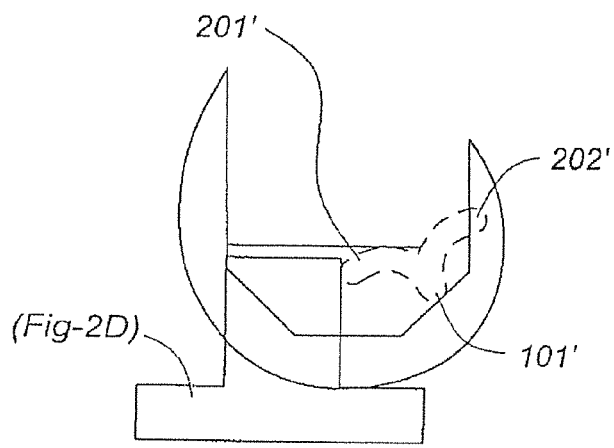
FIG. 2E illustrates the distal femoral component of FIG. 2D and the post configuration of FIG. 6A at full extension.
Figure 2F:
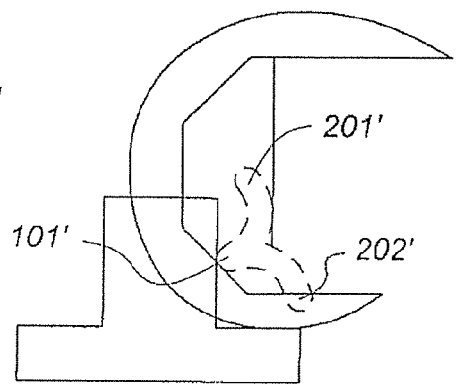
FIG. 2F shows the distal femoral component of FIG. 2D and the post configuration of FIG. 6A at 90 degrees of flexion.
Figure 2G:
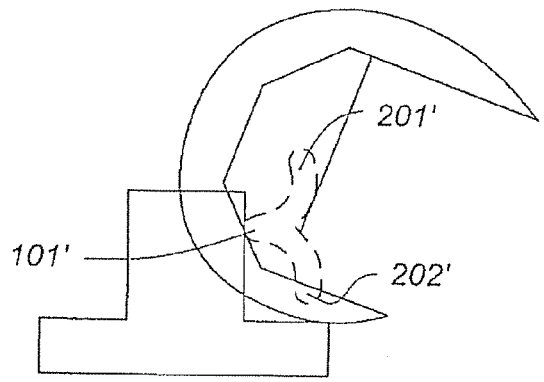
FIG. 2G illustrates the distal femoral component of FIG. 2D and the post configuration of FIG. 6A in flexion beyond 90 degrees.
Figure 2H:
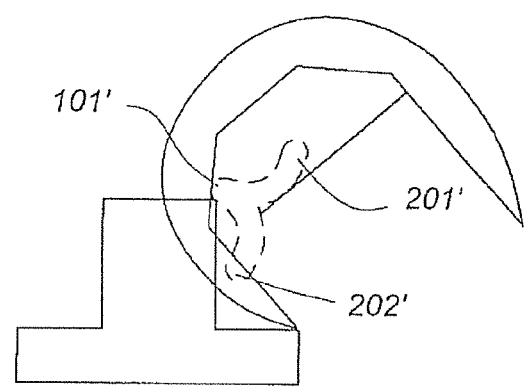
FIG. 2H shows a degree of hyperflexion wherein the extended cam in FIG. 2D first makes contact with the posterior surface of the post.
Figure 2I:
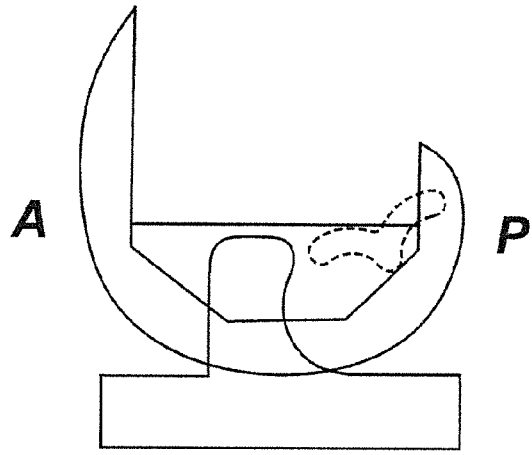
FIG. 2I illustrates the distal femoral component of FIG. 2D and the post configuration of FIG. 6E (with rounded corners) at full extension.
Figure 2J:
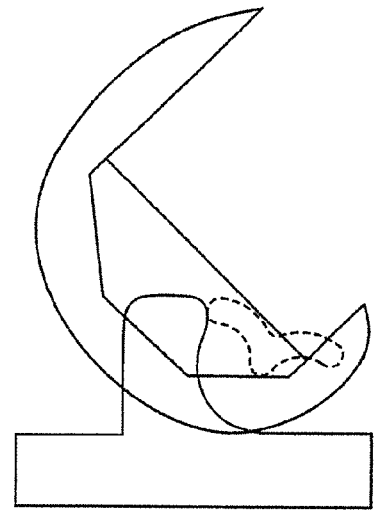
FIG. 2J illustrates the distal femoral component of FIG. 2D and the modified post configuration of FIG. 6E at about 45 degrees of flexion.
Figure 2K:
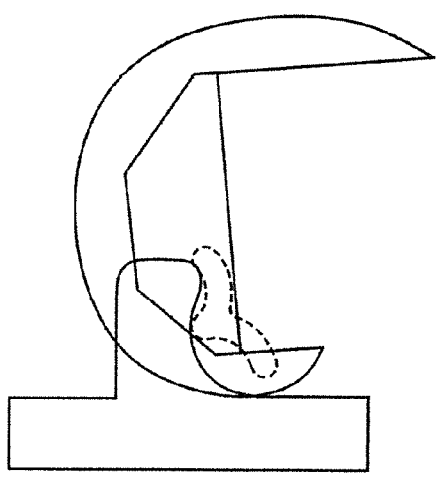
FIG. 2K illustrates the distal femoral component of FIG. 2D and the modified post configuration of FIG. 6E before 90 degrees of flexion.
Figure 2L:
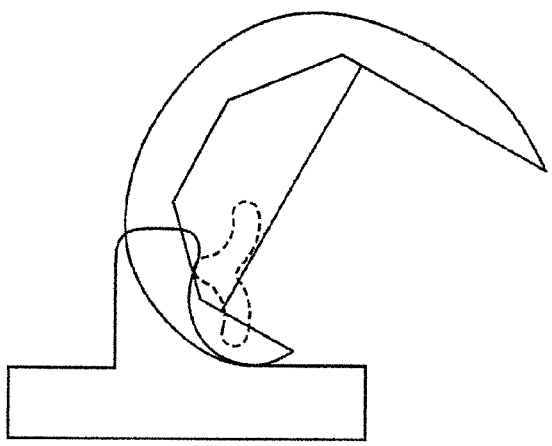
FIG. 2L illustrates the distal femoral component of FIG. 2D and the modified post configuration of FIG. 6E after 90 degrees of flexion.

In FIG. 2B, the cam which is usually present at 101 is engaging the tibial post, cam 201 has disengaged, and cam 202 has not yet engaged but is available for engagement on further flexion. In FIG. 2C, cam 202 is now engaged the post in the presence of additional flexion. Cam 101 can now disengage, cam 201 had disengaged earlier. FIG. 2D illustrates the alternative use of interconnected cams with physically separate contact points.

In FIGS. 2A through 4, the features depicted to provide the various stages of cam/pivoting function are depicted as bars which cross the intercondylar recess or box portion of a cruciate substituting design knee. However, although the terms "cam" or "bar" are used to reference the stages of cam action, it should be understood that the responsible structures may be implemented using any member or combination of elements operative to provide distinct stages of cooperation with the posterior aspect of the superior post. Thus, the members or elements need not be complete or straight across, but may instead be curved, with the post being curved to allow for a rotation, if so desired. The cam structures according to the invention may also be connected to one another forming points of contact as opposed to complete transverse elements. The structure may be provided as part of an open- or closed-type of a box structure, both being familiar to those of skill in the art.

Figure 3:
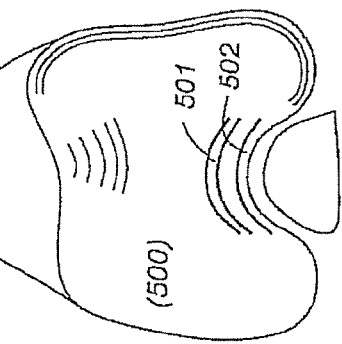
FIG. 3 shows an anterior view of a prior-art cruciate-substituting knee-replacement component.
Figure 4:
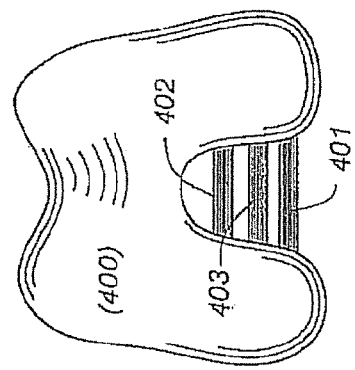
FIG. 4 shows a knee prosthesis according to the invention having multiple cams as seen in a distal-to-proximal view.

Whereas FIGS. 1 and 2 represent lateral or side views of a knee through various ranges of motion, FIG. 3 shows an anterior view of a prior-art cruciate substituting knee component at 300 having an open-type box 302 including a single transverse member 301 for illustrative purposes. FIG. 4 shows a knee prosthesis 400 according to the invention, viewed again from the distal-to-proximal perspective, having three distinct points of cam action. In particular, cam 401 is conventionally located, an anterior cam is disposed at 402 in support of a greater range of enhanced flexion, and a more posterior cam at 403 is used primarily to prevent dislocation of the cams over the post, as discussed above.

Figure 5:
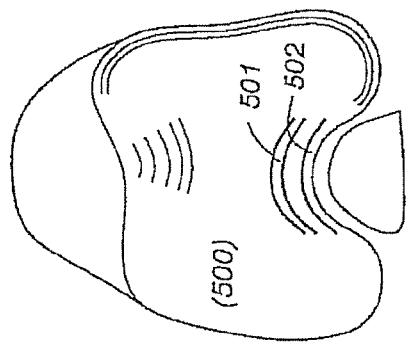
FIG. 5 is a drawing which shows how cam-acting members according to the invention need not be straight across, but may be curved in conjunction with a curved post to facilitate rotation.

FIG. 5 is a drawing which shows various cams from a top view looking down. Note that bars of need not be straight across, but may be curved with the post being curved so that it allows for a rotation to occur if desired. The cam structures according to the invention may be individual distinct bars or may be connected to one another forming points of contact as opposed to distinct structures themselves. It should also be noted that the cam structures may be located at different locations from the posterior to the anterior aspect of the knee design, as well as from the distal or proximal, depending upon implant size, patient physiology, desired range of motion, and other requirements. It should further be noted that as opposed to using three separate cams, one could use two cams intended to contact the posterior aspect of the post or for that matter, use more than three if desired.

Figure 6A:
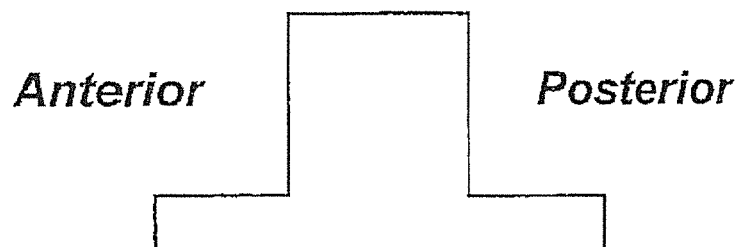
FIGS. 6A through 6E illustrate various alternative post configurations, all of which are applicable to the invention.
Figure 6B:
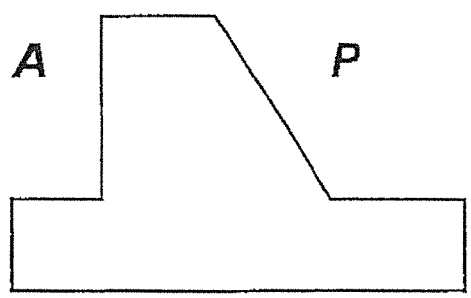
Figure 6C:
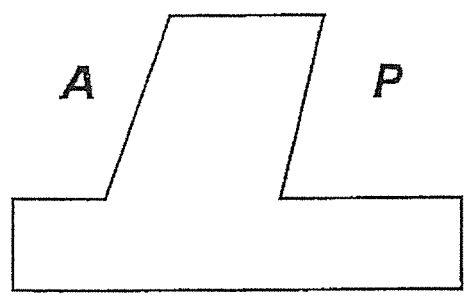
Figure 6D:
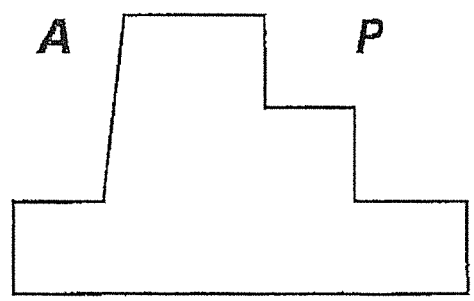
Figure 6E:
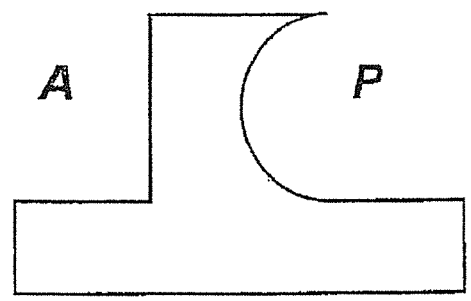

It will also be apparent to one of skill in the art that the posterior aspect of the post may be modified to affect the timing and/or operation of the cam engagement. FIGS. 6A through 6E illustrate various alternative post configurations, all of which are applicable to the invention. As opposed to a substantially straight configuration, as depicted in FIG. 6A, the post may be posteriorly oriented along the posterior aspect, as shown in FIG. 6B. Alternatively, the post may be anteriorly oriented along the posterior aspect, as shown in FIG. 6C. As further alternatives, the post may be stepped, as shown in FIG. 6D, or curved, as shown in FIG. 6E. Also, as opposed to the sharp corners shown, they may be rounded off, and the bars or recesses may be adjusted from the positions shown in FIG. 2 through 5 to achieve a desired operation.

I claim:

1. A total knee replacement system, comprising:
   a tibial component having a tibial post with a posterior surface;
   a femoral component having medial and lateral condylar protrusions which form separated bearing surfaces configured to articulate with the tibial component, the femoral component further including an intercondylar femoral cam mechanism configured to articulate with the posterior surface of the tibial post;
   wherein a majority of the posterior surface of the tibial post is concave in a sagittal plane, defined as a vertical plane extending from front to back;
   wherein the cam mechanism of the femoral component has a superior convex portion, a concave central portion, and an inferior convex posterior portion;
   wherein the inferior convex posterior portion contacts the posterior surface of the tibial post at or before 90 degrees of flexion;
   wherein at least a portion of the posterior surface of the tibial post is convex in a transverse (horizontal) plane; and
   wherein at least a portion of the cam mechanism of the femoral component is concave in the transverse (horizontal) plane.

2. The total knee replacement system of claim 1, wherein a portion of the femoral cam mechanism forms an "s" shaped surface portion in the sagittal plane; and
   wherein the "s" shaped surface portion is formed from the superior aspect of the most superior surface of the femoral cam at its superior convex portion and terminates at the most inferior aspect of the concave surface.

* * * * *